United States Patent [19]

Viera

[11] Patent Number: 5,341,817

[45] Date of Patent: Aug. 30, 1994

[54] ELONGATED GUIDEWIRE FOR USE IN DILATION PROCEDURES

[75] Inventor: Fernando M. Viera, Hialeah, Fla.

[73] Assignee: Cordis Corporation, Miami Lakes, Fla.

[21] Appl. No.: 990,069

[22] Filed: Dec. 14, 1992

[51] Int. Cl.$^5$ ................................. A61B 5/00
[52] U.S. Cl. ............................................ 128/772
[58] Field of Search ............... 128/657, 772; 604/95, 604/283

[56] References Cited

U.S. PATENT DOCUMENTS

| | | | |
|---|---|---|---|
| 2,217,188 | 10/1940 | Snyder | 343/901 |
| 2,456,330 | 12/1948 | Scott | 343/901 |
| 2,491,601 | 12/1949 | Bernstein et al. | 343/901 |
| 3,631,848 | 1/1972 | Mueller . | |
| 4,498,482 | 2/1985 | Williams | 128/786 |
| 4,619,274 | 10/1986 | Morrison | 128/772 |
| 4,649,916 | 3/1987 | Frimberger . | |
| 4,664,120 | 5/1987 | Hess | 128/642 |
| 4,676,249 | 6/1987 | Arenas et al. | 128/657 |
| 4,719,924 | 1/1988 | Crittenden et al. | 128/772 |
| 4,827,941 | 5/1989 | Taylor et al. | 128/657 |
| 4,846,193 | 7/1989 | Tremulis et al. | 128/772 |
| 4,854,330 | 8/1989 | Evans, III et al. | 128/772 |
| 4,895,168 | 1/1990 | Machek | 128/772 |
| 4,917,102 | 4/1990 | Miller et al. | 128/657 |
| 4,922,923 | 5/1990 | Gambale et al. | 128/772 |
| 4,966,163 | 10/1990 | Kraus et al. | 128/772 |
| 4,988,356 | 1/1991 | Crittenden et al. | 606/192 |
| 5,188,621 | 2/1993 | Samson | 128/772 |
| 5,195,535 | 3/1993 | Shank . | |

*Primary Examiner*—Max Hindenburg
*Attorney, Agent, or Firm*—Watts, Hoffmann, Fisher & Heinke

[57] ABSTRACT

An extendable guidewire for insertion within a subject. The guidewire includes an elongated flexible member having a diameter small enough for insertion into a subject and includes an outer member and an inner member. A central passageway extends through a proximal portion of the outer member. The inner member comprises a guidewire extension that is dimensioned to fit within the central passageway for back-and-forth movement with respect to the outer member. The outer member has a movement-limiting portion at its proximal end that cooperates with a movement-limiting portion of the inner member to limit movement of the inner member and frictionally hold the inner member in its extended position.

5 Claims, 3 Drawing Sheets

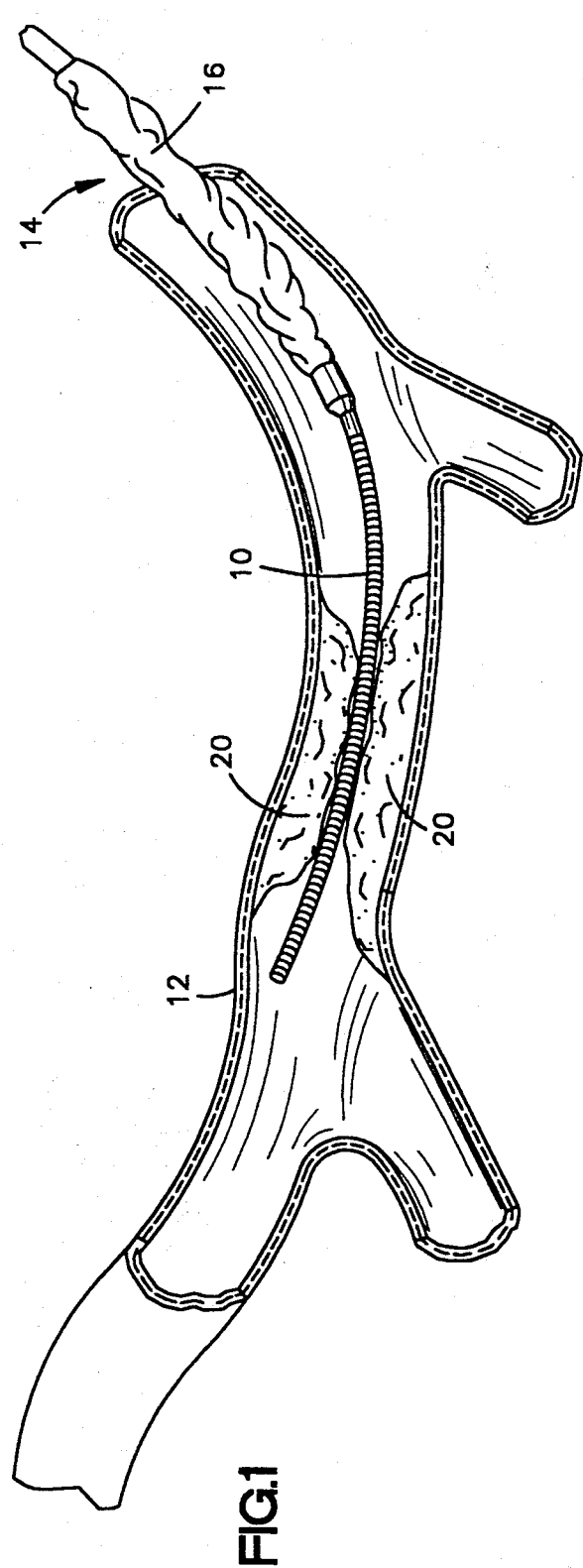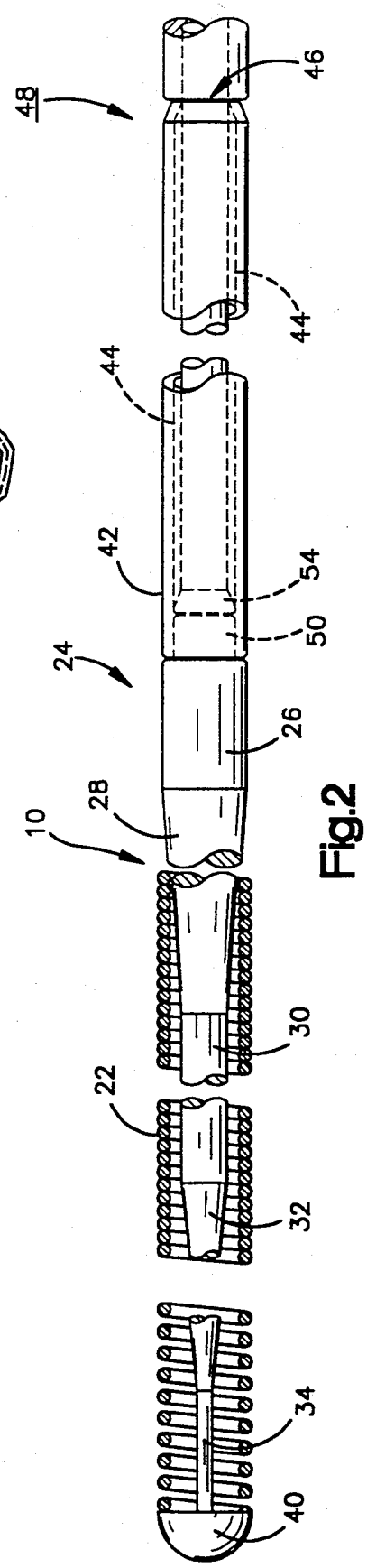

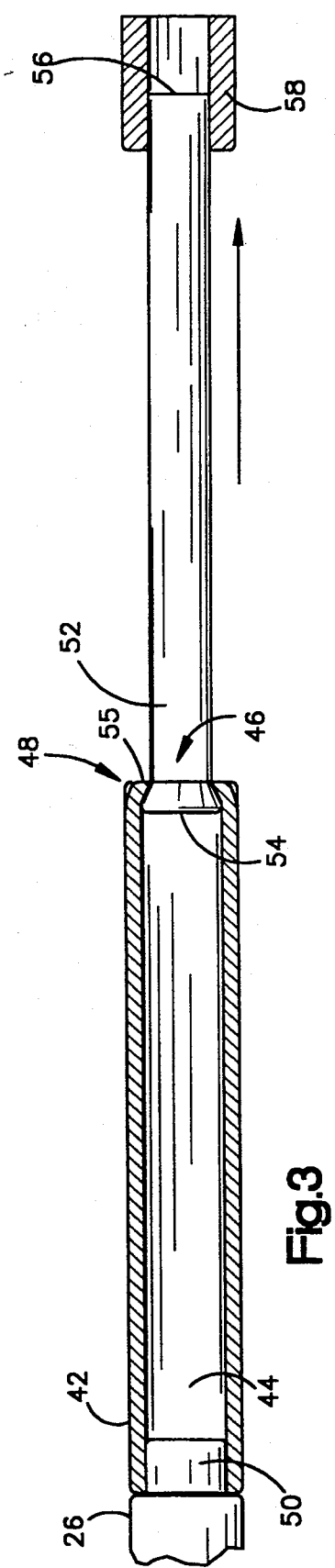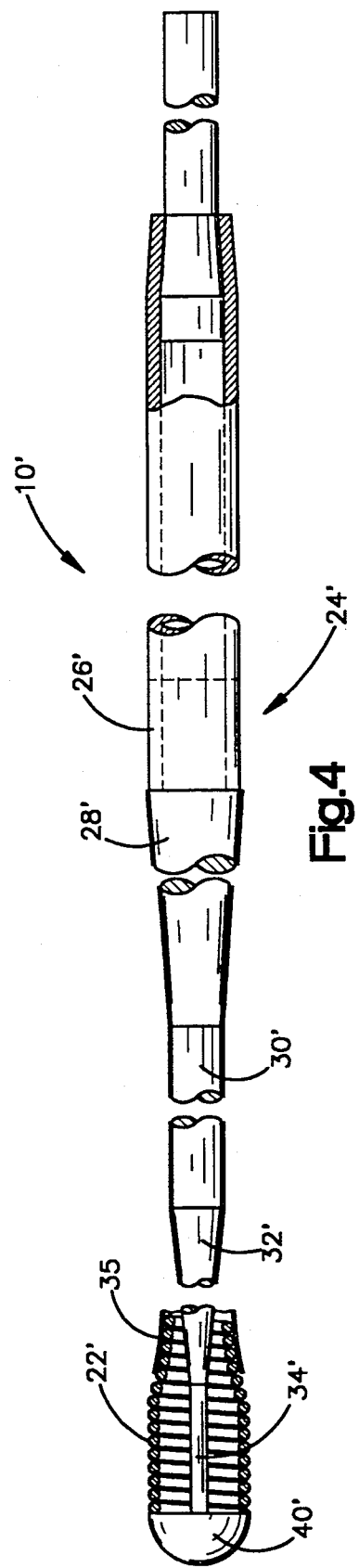

ELONGATED GUIDEWIRE FOR USE IN DILATION PROCEDURES

TECHNICAL FIELD

The present invention relates to a flexible elongated guidewire used to position a catheter within a subject and more particularly concerns a guidewire particularly useful in exchanging dilation catheters.

BACKGROUND ART

Percutaneous angioplasty is a therapeutic medical procedure that can increase blood flow through a blood vessel. It can sometimes be used as an alternative to coronary by-pass surgery, for example. An elongated catheter having a deflated balloon at its distal end is guided through a patient's cardiovascular system to the coronary artery of the heart. The balloon is inflated to compress deposits that have accumulated along the inner walls of the coronary artery to widen the artery lumen and increase blood flow.

A known technique for positioning the balloon catheter uses an elongated guidewire that is inserted into the patient and routed through the cardiovascular system as guidewire progress is viewed on an x-ray imaging screen.

Representative prior art patents that disclose flexible, elongated guidewires are U.S. Pat. No. 4,545,390 to Leary, U.S. Pat. No. 4,538,622 to Samson et al. and U.S. Pat. No. 3,906,938 to Fleischhacker and U.S. Pat. 4,846,186 to Box et al. The Box et al. patent is incorporated herein by reference.

Occasionally, during the performance of an angioplasty procedure, the physician determines a different catheter is needed for the particular procedure. This can occur, for example, if the size of the catheter is not appropriate for the particular blood vessel blockage that is being treated.

It also may be necessary to exchange catheters if difficulty is encountered in pushing the catheter through a lesion. If a guidewire can be guided through the lesion but the catheter balloon cannot, the physician may decide to withdraw the catheter and insert a smaller diameter catheter to bridge the lesion with the smaller balloon. If the smaller balloon is successfully placed, it is inflated to create a larger passageway through the lesion and then the larger diameter catheter may be reinserted and used to widen the passageway even further. When exchanging catheters, it is important that the guidewire tip not be retracted from its position. If the guidewire is removed from the lesion, the limited passage may close due to a blood vessel spasm so that the guidewire cannot again be pushed through the lesion.

U.S. Pat. No. 4,872,941 to Taylor et al. concerns an extendable guidewire system for introducing a dilatation catheter into a cardiovascular system. The guidewire has a guidewire section and extension section with a connection for joining the two sections. The guidewire section is used for positioning the catheter within the subject, and the extension section can be used to extend the length of the guidewire for use in exchanging catheters. The structure shown in the '941 patent uses separate parts which must be assembled when an exchange of catheters is deemed appropriate.

U.S. Pat. No. 4,846,193 to Tremulis et al. concerns an extendable guidewire and method for introducing and exchanging catheters in vascular procedures such as coronary angioplasty. The guidewire has first and second interfitting sections movable between extended and retracted positions.

DISCLOSURE OF THE INVENTION

The present invention concerns a guidewire for insertion within a subject. The guidewire can be lengthened by grasping a small diameter extension and withdrawing it from within a central passageway passing through a guidewire sheath which extends inside a subject. The guidewire is used to help position a catheter within the subject. The extension can be moved back and forth with respect to this outer sheath by pulling or pushing the extension. The outer member or sheath has a movement-limiting portion at its proximal end that cooperates with a movement-limiting portion of the extension to prevent movement of the extension with respect to the sheath as a catheter is withdrawn from a subject. This is most preferably accomplished with beveled or chambered surfaces on both the sheath and extension which lock together along a segment of the guidewire due to frictional engagement.

During initial insertion of the catheter, the small diameter inner member fits almost completely within the central passageway of the outer member. If a catheter exchange is desired, the inner member is withdrawn from the central passageway to extend the length of the guidewire and allow the first catheter to be withdrawn while maintaining the position of the guidewire's distal tip within the subject.

A guidewire constructed in accordance with the present invention facilitates the process of exchanging catheters within a subject. The guidewire is first moved into the subject to help in routing a first catheter to a position within a subject. When the physician determines a different catheter is needed, the inner member of the extendable guidewire is withdrawn to increase the combined length of the inner and outer members. The first catheter can then be removed from the subject without losing control of the guidewire, and a second catheter inserted into the subject by placing the second catheter over the guidewire and routing the catheter along the guidewire into the subject.

Other objects, advantages and features of a guidewire constructed in accordance with the invention can be better understood by reference to a detailed description of a preferred embodiment of the invention that is described in conjunction with the accompanying drawings.

BRIEF DESCRIPTION OF THE DRAWINGS

FIG. 1 is a schematic depiction of a section of a partially occluded blood vessel;

FIG. 2 is a partially sectioned elevation view of an extendable guidewire;

FIG. 3 is a partially sectioned view of the FIG. 2 guidewire showing elongation of the guidewire;

FIG. 4 is a partially sectioned elevation view of an alternate embodiment of an extendable guidewire;

BEST MODE FOR PRACTICING THE INVENTION

Figure 5:
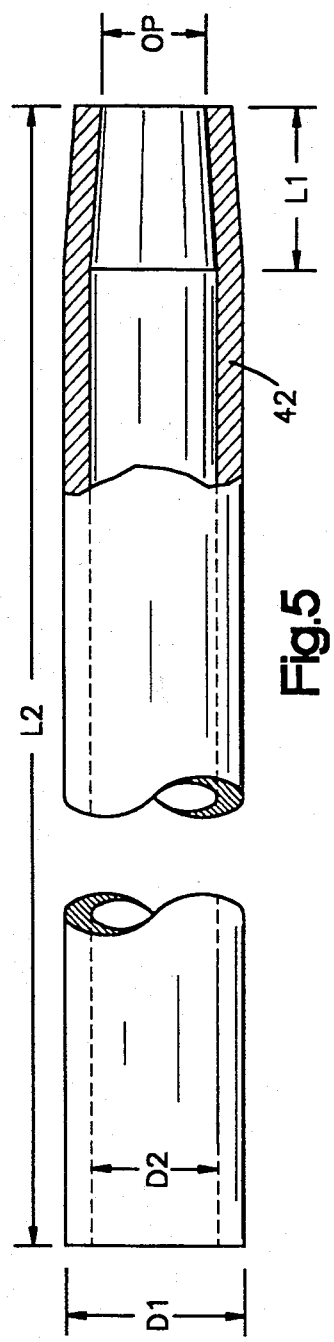
FIGS. 5 and 6 are enlarged partially sectioned views of relatively movable inner and outer guidewire members.

Turning now to the drawings, FIG. 1 depicts an elongated guidewire 10 positioned within a subject blood vessel 12. The guidewire 10 is used in positioning a balloon catheter 14 that includes a distally located inflatable balloon 16. The balloon catheter includes a passageway extending through its length to accommodate the guidewire 10. In a typical angioplasty procedure, both the balloon catheter and guidewire are routed into a subject within a guide catheter (not shown) and pushed beyond a distal tip of the guide catheter. The guidewire and balloon catheter are then moved forward in a coordinated manner to push the balloon 16 through deposits 20 within the vessel.

In FIG. 1, the guidewire has been inserted between the deposits 20 and the balloon catheter is being pushed into the subject so that the balloon 16 can be inflated against the deposits 20 for compressing those deposits against the inner wall linings of the blood vessel. This procedure has been utilized with success to enlarge passageways through partially occluded blood vessels.

FIG. 2 is a partially sectioned elevation view of the guidewire 10 showing a spring coil 22 attached to a guidewire core 24. Proximal to the spring 22, the guidewire core includes a portion 26 having a uniform diameter, cylindrical outer surface. The guidewire core tapers along a portion 28 to a second uniform diameter portion 30 spaced from the spring coil 22. A second tapered portion 32 narrows to a yet smaller diameter segment 34 at the extreme distal end of the guidewire. The segment 34 is flattened at its extreme distal tip and attached to the spring 22 by a hemispherical weld 40. At the proximal end of the spring 22, a solder joint of surgical grade solder connects the guidewire core 24 and the spring coil 22. In the FIG. 2 embodiment, this solder connection is preferably located where the core 24 begins to taper at the proximal end of the segment 28.

FIG. 4 is a partially sectioned elevation view of an alternate guidewire 10' showing a spring coil 22' attached to a guidewire core 24'. Proximal to the spring 22', the guidewire core includes a portion 26' having a uniform diameter, cylindrical outer surface. The guidewire core tapers along a portion 28' to a second uniform diameter portion 30'. A second tapered portion 32' narrows to a yet smaller diameter segment 3' at the extreme distal end of the guidewire. The segment 34' is flattened at its extreme distal tip and attached to the spring 22' by a hemispherical weld 40'. A plastic sleeve 35 overlies a tapered portion of the spring coil 22' and helps hold the spring 22' in place.

In both the FIG. 2 and FIG. 4 embodiments, the guidewire's distal tip is pre-bent to a desired configuration to facilitate routing of the guidewire through the subject's cardiovascular system into an appropriate region of the blood vessel such as the coronary artery.

Each guidewire core 24' is attached to a generally annular guidewire segment or sheath 42. The segment 42 defines a central passageway 44 that extends the length of the segment 42 to an opening 46 at an end 48 of the segment 42.

The segment 42 is preferably connected to the core portion 26 by welding the segment 42 to a reduced diameter portion 50 of the guidewire core that extends a short distance into the central passageway 44. As is evident from FIGS. 2 and 3, the reduced diameter portion 50 has a diameter slightly less than the diameter of the central passageway 44.

An elongated stainless steel extension 52 is dimensioned to fit within the central passageway 44 of the body portion 42. In the preferred embodiment, the guidewire extension 52 is dimensioned slightly smaller than the central passageway 44 and includes a movement-limiting portion or stop 54 at its distal tip that is larger in diameter than the rest of the extension 52. The opening 46 at the end 48 has a reduced diameter when compared to the diameter of the central passageway 44. The guidewire extension 52 moves back and forth within the central passageway 44 and through the opening 46, but the stop 54 is unable to pass through the opening 46 since it contacts the reduced diameter portion of the passageway. This contact prevents separation of the guidewire extension 52 from the body portion or sheath 42 and also holds the extension in the extended position as the attending physician withdraws the catheter.

Attached to a proximal end 56 of the guidewire extension 52 is a handle 58. The handle 58 is grasped by a user of the guidewire 10 during use of the guidewire.

Figure 7:
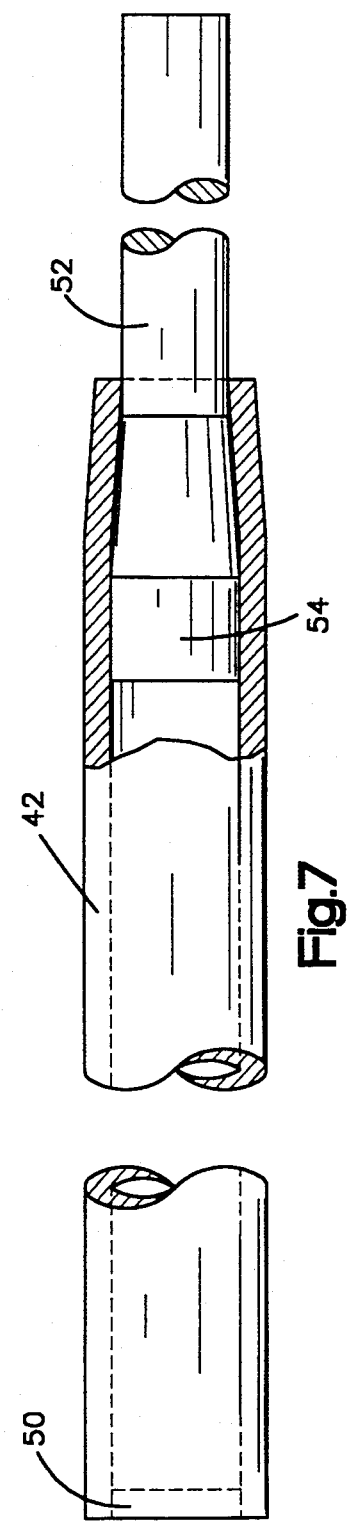
FIG. 7 is an enlarged partially sectioned view showing the FIGS. 5 and 6 members engaging each other.

As seen most clearly in the enlarged view of FIG. 7, the distal end of the extension 52 and proximal end of the segment 42 engage to impede relative movement between the two as the catheter 14 is withdrawn from a subject. Swaging reduces the extreme proximal end of the central passageway to a lesser inner diameter than the remaining portion. This is accomplished by putting a 14/1000 inch outer diameter tube having 10.5/1000 inner diameter into a die and swaging the tube to cause the inner diameter to decrease by approximately 1/1000. This occurs over a ¼ inch segment L1 of the proximal section. The extension 52 is ground along most of its length and a champer created over approximately ¼ inch of its distal end. The champered portion L' of the extension 52 engages the swaged portion of the sheath 42 to lock the two together. No twisting or turning of the extension is needed to provide this locking. If the physician wants to reinsert the extension 52 after a catheter exchange takes place, the engagement can be released by pushing inward on the extension 52.

Figure 6:
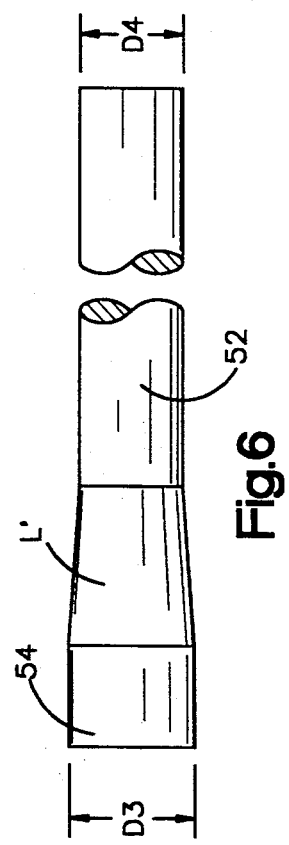

Table I (below) lists the dimensions of the body portion 42 and guidewire extension 52 depicted on FIGS. 5 and 6:

TABLE I

|  | Designation | Dimension (Inches) |
| --- | --- | --- |
| Inner Diameter Sheath | D2 | .0105 + .0002 − .00 |
| Outer Diameter Sheath | D1 | .0140 |
| Opening Diameter Sheath | OP | .0093 + .0003 − .0000 |
| Length Sheath | L2 | 57.875 ± .050 |
| Taper Sheath and Extension | L1 | .250 |
| Stop Diameter, Extension | D3 | .0100 ± .0002 |
| Extension Diameter | D4 | .0090 ± .0002 |

During use, typically during the performance of an angioplasty procedure, the guidewire 10 is routed through the patient's blood vessel 12 in order to position the balloon catheter 14 relative to deposits 20 within the blood vessel 12. If, during the performance of the procedure, a physician determines that a different catheter is needed for the particular procedure, he or she grasps the handle 58 and pulls on the guidewire extension 52 to slide it out of the body portion 42 thereby increasing the overall length of the guidewire 10. A combined length of the body portion 42 and the extension 52 is long enough to allow the balloon catheter 14 to be completely removed from the patient while the guidewire's distal end continues to bridge the deposits 20. Once the catheter 14 is removed from the patient, the extension 52 can be pushed back into the guidewire body and a replacement catheter routed over the guidewire 10 to position a balloon, for example, relative the deposits at the guidewire's distal end.

The substitution of the catheter can therefore be performed without losing control of the guidewire 10. Also, the guidewire 10 is assembled and does not require the attachment of separate parts that must be attached when replacement of the original catheter is deemed appropriate.

Although the preferred embodiment of this invention has been shown and described, it should be understood that various modifications and re-arrangements of the parts may be resorted to without departing from the scope of the invention as disclosed and claimed herein.

I claim:

1. A guidewire for insertion into a subject blood vessel, said guidewire comprising:
    a flexible tip;
    an elongated flexible body having a distal end for supporting said tip and defining a central passageway having a first portion which extends through the body with a substantially uniform inner diameter and having a second portion which tapers uniformly to an opening with a lesser inner diameter at a proximal end of the body; and
    an elongated extension for reciprocal movement relative to said body and having a central portion dimensioned to fit through the opening in said body, a distal end portion dimensioned to fit within the central passageway of said body and to engage said second portion of said body to limit relative movement in one direction between said extension and said body and an intermediate portion between said central portion and said end portion, said intermediate portion is tapered for frictional engagement with said second portion of said body over a circumferential extent and an axial extent to inhibit separation of said extension and said body.

2. The guidewire in claim 1 wherein said end portion of said extension is cylindrical in shape and has a longitudinal extent within the passageway of said body to maintain a coaxial relationship between said body and said extension.

3. The guidewire in claim 1 wherein said intermediate portion of said extension comprises a frusto-conical outer surface and wherein said second portion of said body comprises a frusto-conical inner surface.

4. The guidewire in claim 1 wherein said intermediate portion of said extension and said second portion of said body each have a longitudinal extent of approximately 0.25 inch.

5. A guidewire for insertion into a subject blood vessel, said guidewire comprising:
    a flexible tip;
    an elongated flexible body having a distal end for supporting said tip and defining a central passageway having a first portion which extends through the body with a substantially uniform first inner diameter and having a second portion with a frusto-conical inner surface which tapers uniformly to an opening with a second inner diameter at a proximal end of the body, the second inner diameter is less than the first diameter; and
    an elongated extension for reciprocal movement relative to said body and having a central portion dimensioned to fit through the opening in said body, a distal end portion dimensioned to fit within the central passageway of said body and to engage said second portion of said body to limit relative movement in one direction between said extension and said body and an intermediate portion between said central portion and said end portion,
    said intermediate portion having a frusto-conical outer surface for frictional engagement with said second portion of said body over a circumferential extent and an axial extent to inhibit separation of said extension and said body, said end portion of said extension is cylindrical in shape and has a longitudinal extent within the passageway of said body to maintain a coaxial relationship between said body and said extension, and said intermediate portion of said extension and said second portion of said body each have a longitudinal extent of approximately 0.25 inch.

* * * * *